United States Patent
Schmidt et al.

(10) Patent No.: US 10,352,754 B2
(45) Date of Patent: Jul. 16, 2019

(54) PROBE UNIT

(71) Applicant: Endress+Hauser GmbH+Co. KG, Maulburg (DE)

(72) Inventors: Robert Schmidt, Schopfheim (DE); Andreas Krumbholz, Maulburg (DE); Armin Wernet, Rheinfelden (DE); Kaj Uppenkamp, Wehr (DE)

(73) Assignee: Endress+Hauser SE+Co. KG, Maulburg (DE)

( * ) Notice: Subject to any disclaimer, the term of this patent is extended or adjusted under 35 U.S.C. 154(b) by 213 days.

(21) Appl. No.: 15/534,833

(22) PCT Filed: Nov. 9, 2015

(86) PCT No.: PCT/EP2015/076005
§ 371 (c)(1),
(2) Date: Jun. 9, 2017

(87) PCT Pub. No.: WO2016/091497
PCT Pub. Date: Jun. 16, 2016

(65) Prior Publication Data
US 2017/0343407 A1 Nov. 30, 2017

(30) Foreign Application Priority Data
Dec. 12, 2014 (DE) .................. 10 2014 118 547

(51) Int. Cl.
*G01F 23/24* (2006.01)
*G01F 23/26* (2006.01)
*G01N 27/07* (2006.01)

(52) U.S. Cl.
CPC .......... *G01F 23/242* (2013.01); *G01F 23/268* (2013.01); *G01N 27/07* (2013.01)

(58) Field of Classification Search
CPC ..... G01F 23/242; G01F 23/243; G01F 23/268
See application file for complete search history.

(56) References Cited

U.S. PATENT DOCUMENTS

| 6,945,120 B1 | 9/2005 | Marcus et al. |
| 2013/0276532 A1 | 10/2013 | Kato |
| 2013/0333466 A1* | 12/2013 | Schmidt ............... G01F 23/242 73/304 C |

FOREIGN PATENT DOCUMENTS

| CN | 103403505 A | 11/2013 |
| DE | 3036347 A1 | 5/1981 |

(Continued)

OTHER PUBLICATIONS

Search Report for German Patent Application No. 10 2014 118 547.1, German Patent Office, dated Jul. 30, 2015, 10 pp.

(Continued)

*Primary Examiner* — David M. Gray
*Assistant Examiner* — Andrew V Do
(74) *Attorney, Agent, or Firm* — Christopher R. Powers; PatServe (57) ABSTRACT

A probe unit having a coaxial structure and including a probe electrode, a guard electrode and a contacting module arranged on a section of the probe electrode, which contacting module including an insulating sleeve, a flexible circuit board with a first conduction path for the electrical contacting of the probe electrode and a second conduction path for the electrical contacting of the guard electrode, and a module housing, wherein a first contact plate is provided that electrically contacts the first conduction path, the module housing including a second contact plate that electrically contacts the second conduction path, wherein the module housing has a pot-shaped geometry with a cylindrical wall, which wall substantially surrounds, protects and/or electromagnetically shields at least the probe electrode in the region in which the contacting module is arranged, at least a part of the insulating sleeve, and at least sections of the circuit board.

13 Claims, 7 Drawing Sheets

(56) References Cited

FOREIGN PATENT DOCUMENTS

| | | |
|---|---|---|
| DE | 3211385 A1 | 8/1983 |
| DE | 3212434 C2 | 10/1983 |
| DE | 102011004807 A1 | 8/2012 |
| DE | 102011086216 A1 | 5/2013 |
| EP | 1378014 B1 | 1/2004 |
| EP | 2340420 A1 | 5/2010 |
| WO | 9737198 A1 | 10/1997 |
| WO | 2012116851 A1 | 9/2012 |

OTHER PUBLICATIONS

Search Report for International Patent Application No. PCT/EP2015/076005, WIPO, dated Feb. 26, 2016, 16 pp.

* cited by examiner (PRIOR ART)

PROBE UNIT

CROSS-REFERENCE TO RELATED APPLICATION

The present application is related to and claims the priority benefit of German Patent Application No. 10 2014 118 547.1, filed on Dec. 12, 2014 and International Patent Application No. PCT/EP2015/076005, filed Sep. 11, 2015, the entire contents of which are incorporated herein by reference.

TECHNICAL FIELD

The present disclosure relates to a probe unit having at least a section-by-section coaxial structure. In particular, the present disclosure relates to a probe unit for a device for capacitively and/or conductively determining of at least one process variable of a medium in a container. The process variable is, for example, the fill-level and/or the electrical conductivity and/or the permittivity of the medium.

BACKGROUND

Field devices based upon the capacitive or conductive principle generally have a substantially cylindrical probe unit with at least one probe electrode which can be introduced into the container. For level measurement, rod-shaped probe units extending vertically into the container are known for continuous measurement and, on the other hand, probe units, which can be introduced into the wall of the container, are also known for measuring the level.

In addition, a supplementary electrode, especially a so-called guard electrode, is often used to avoid deposit formation on the probe electrode. The electrode, which coaxially surrounds the probe electrode, is separated from the probe electrode by means of an insulation, and is at the same electrical potential as the probe electrode, as described in, for example, DE 32 12 434 C2. In particular, probe units for point-level measurement are frequently designed in such a way that the probe electrode is at least coaxially surrounded by a guard electrode in the section of the process connection.

The underlying measurement principles of capacitive and conductive level measurement are known from a large number of publications.

In the conductive measuring method, the fill-level is monitored by detecting whether an electrical contact exists between a probe electrode and the wall of a conductive container or a second electrode via a conductive medium. Corresponding field devices are, for example, produced and marketed by the Applicant under the trade name Liquipoint. However, the conductive measuring principle reaches its limits for electrical conductivities $\leq 0.5$ μS/cm, since a change in the conductivity of the medium relative to the conductivity of air is then too small to be reliably detected by the measuring electronics. Media that are difficult to monitor using a conductive measuring method include, for instance, distilled water, molasses, or alcohols. Media with an electrical conductivity of less than 1 μS/cm and a dielectric constant of less than 20 are also problematic. In particular, oils and gases fall into this area.

The capacitive measuring principle is suitable here. The fill-level of the medium in a container is here determined from the capacitance of the capacitor formed by a probe electrode and the wall of the container or a second electrode. Depending upon the conductivity of the medium, either the medium itself or an insulation of the probe electrode forms the dielectric of the capacitor. Field devices based upon the capacitive measuring principle are also produced and marketed by the Applicant in many different configurations, e.g., under the trade names Liquicap or Solicap. Although the fill-level measurement by means of a capacitive measuring method is possible in principle for conductive and non-conductive media, an insulation of the measuring probe is necessary for media with an electrical conductivity >50 μS/cm, which can lead to various disadvantages for the measurement.

Since the advantages and disadvantages of the capacitive and conductive measuring method conflict, a so-called multi-sensor is advantageous, which can determine the fill-level in both a conductive and a capacitive operating mode. By using such a sensor, the level measurement is independent of the electrical properties of the medium. However, various points must be considered when designing such a multi-sensor.

For example, the achievable measuring resolution in the capacitive operating mode is determined by the geometric design of the probe unit. If, for example, the probe unit is designed such that it essentially closes with it after installation in the wall of the container, as in the case of the field device marketed by the Applicant under the trade name FTW33, the measured capacitances can lie in the femtofarad range. If, on the other hand, the measuring probe protrudes at least partially into the container, the measured values for the capacitance are up to several orders of magnitude above this. It goes without saying that the measured capacitances also depend, among other things, upon the medium properties, but these dependencies are to be considered application-specific and, therefore, secondary to the question of the construction of a suitable probe unit.

A further point relates to an electronic unit which is connected to the probe unit and which is used for detection, supply, and/or evaluation of the signal. The components used for this must be adapted to the respective measuring ranges to be expected. This applies, in particular, to the capacitive operating mode, in which capacitances in the femtofarad range have to be detected, which places the highest demands on the electronics unit used.

Finally, a decisive point for the construction of a multi-sensor is given by the contacts of the probe electrode and the additional electrode, as well as their connection to the electronics unit. Cables with strands for electrode contacts are most often used. In doing so, the strands are soldered to the elements to be contacted, while the various cables lead into a common plug. A more elegant method has been disclosed in EP1378014B1 and describes the use of flexible circuit boards for contacting piezoelectric elements arranged in a stack. For this purpose, the flexible printed circuit board has a plurality of contact lugs, which can be glued by bending the piezoelectric elements. This solution is, in particular, more space-saving than the use of cables with strands, but is difficult and complicated in production.

A simpler contacting possibility using a flexible printed circuit board has been disclosed in DE 102011086216A1. A probe unit which is typical of the capacitive and/or conductive mode of operation is described with a contacting module by means of which the probe electrode and the additional electrode are contacted via the flexible printed circuit board. The contacting module has an insulating sleeve and a module housing. The insulating sleeve is designed to receive a section of the rod-shaped probe electrode and to accommodate the flexible printed circuit board. For this purpose, the insulating sleeve has a supporting element, which serves to support two contact regions of the printed circuit board, and which at the same time ensures electrical separation between the two contact regions of the printed circuit board. The module housing holds the assembly together, and, in particular, serves to affix the two contact regions of the flexible printed circuit board. It is made of an electrically insulating material, for example, of a plastic material.

In such a contacting module, the electrode located inside the coaxial structure of the probe unit thus serves as a holder for the contacting module, for which purpose it is not surrounded by the external electrode at least on a section whose length corresponds to the height of the contacting module and a fastening means. The insulation between the probe electrode and the additional electrode can be realized by an element made of an electrically insulating material such as plastic, glass, or else in the form of an air gap.

Since the probe housing serves as a ground potential, however, capacitances between the probe electrode and the probe housing can occur in the region in which the probe electrode is not surrounded by the additional electrode. This leads to interfering influences during the signal transmission from the probe unit to the electronics unit. The shorter the probe unit, the more significant the interfering influences are. In particular, in the case of such probe units, in the installed state essentially complete with the wall of the container as in the case of the aforementioned FTW33, for example, in which the measured capacitances can lie in the femtofarad range, a correct detection of the measured capacitances can be prevented by the interference influences.

SUMMARY

The present disclosure is based upon the aim of providing a simple contacting possibility for a probe unit having at least a section-by-section coaxial structure, by means of which a complete electrical shielding of the probe electrode is ensured.

This aim is achieved by a probe unit having the characteristics of claim 1. Advantageous embodiments of the probe unit are the subject matter of the dependent claims.

The probe unit includes at least a probe housing, an at least section-wise, rod-shaped probe electrode an additional electrode which at least partially coaxially surrounds the probe electrode and is separated from the probe electrode by electrical insulation, a first fastening means by means of which the additional electrode is affixed in the probe housing, a contacting module which can be applied to a rod-shaped section of the probe electrode arranged in the probe housing, and a second fastening means for attaching the contacting module to the probe electrode, wherein the contacting module comprises at least the following components: an insulating sleeve which has a substantially cylindrical base body for receiving a portion of the rod-shaped probe electrode and a two-dimensional support element which is essentially orthogonal to the base body and divides the base body into a first section and a second section, a flexible printed circuit board having at least a first conductor track for electrically contacting the probe electrode and a second conductor track for electrically contacting the additional electrode, the flexible printed circuit board having, in an end region, a first contact region into which the first conductor track opens, wherein the first contact region and the second contact region each have a central recess whose diameter is at least equal to the outer diameter of the base body of the insulating sleeve, and wherein at least the central recesses of the first contact region and the second contact regions are formed by folding the printed circuit board in such a way that the first contact region can be applied to the first portion of the base body, and the second contact region can be applied to the second portion of the base body, and a module housing.

Furthermore, it is provided according to the present disclosure that the probe unit has a first contact disc, which first contact disc can be applied to the first section of the base body of the insulating sleeve and electrically contacts the first conductor track in the first contact region. the module housing has a second contact disc, which first contact disc can be applied to the second section of the base body of the insulating sleeve and electrically contacts the second conductor track in the second contact region. The module housing has a pot-shaped geometry, with a cylindrical wall which extends parallel to the base body from the second contact disc, where the wall has at least the probe electrode in the region in which the contacting module is applied, the insulating sleeve is arranged at least in the region of the supporting element, and the flexible circuit board at least substantially surrounds, protects, and/or shields against electromagnetic radiation in the region of the two contact regions, and the first contact disc has a smaller outer diameter than the second contact disc.

The present disclosure is suitable in principle for all probe units with two elements to be contacted, which are at least partially arranged in a coaxial configuration. However, the present disclosure is particularly suitable for probe units of devices for capacitively or conductively determining and/or monitoring at least one process variable of a medium in a container.

The supporting element serves as a two-dimensional contact surface of the two contact regions of the flexible printed circuit board. At the same time, it ensures an electrical separation between the two contact regions, which are preferably connected in an annular manner and by way of a web, so that the two recesses can be positioned one above the other via the first contact region by folding over the second contact region. The two sections into which the support element divides the base body of the insulating sleeve can be identical or different in length.

Both the first contact disc and the module housing are made of an electrically conductive material. Since the electrode located within the coaxial structure the probe electrode, which is located inside the coaxial structure serves as a support for the contact-making module due to the simplicity of the construction of the contacting possibility, it is not surrounded at all by the external electrode in the region in which the contacting module is located. In this region, according to the present disclosure, the module housing with its pot-shaped configuration ensures complete electromagnetic shielding of the probe electrode in such a way that the interfering influences described above can be avoided. This is of great importance, in particular, in the case of short probe units, including in those which essentially terminate flush with the wall of the container.

In addition to the electromagnetic shielding effect, the contacting module according to the present disclosure is distinguished by a space-saving, compact, and simple design, which in turn is particularly important in the case of probe units which terminate essentially flush with the wall of the container.

The solution according to the present disclosure is also cost-effective in production and in material requirements.

For the insulation between the probe electrode and the additional electrode, an element made of an electrically insulating material, such as plastic or glass, or in the form of an air gap may be provided. A combination of these two variants is also possible. Finally, the probe housing may be metallic and serves as a mass potential.

In a first embodiment, the flexible printed circuit board is a semiflex printed circuit board, for example, a circuit board composed of at least two layers, with a first layer in which the first conductor track runs at least in sections and a second layer in which at least the second conductor track runs at least in sections. The choice of a semiflex circuit board offers the best compromise between stability and bending stiffness.

In a first variant, the flexible printed circuit board is a three-layer circuit board with a first layer, a second layer and a third layer, wherein the second layer is arranged between the first layer and the third layer, wherein the first conductor track runs in the second layer, wherein the second conductor track at least in the area up to the two contact regions is subdivided into a first branch and a second branch, and wherein the first branch of the second conductor track runs in the first layer, and wherein the second branch of the second conductor track runs in the third layer. The measuring signal of the probe electrode thus runs along the middle layer, while the signal of the additional electrode is guided in the upper and lower layers. The choice of a three-layered printed circuit board therefore allows electromagnetic shielding of the probe electrode against the probe housing also in the region of the flexible printed circuit board, which is not located within the module housing.

In a second variant, the flexible printed circuit board is a two-layered printed circuit board with a first layer and a second layer, and a first and second partial area with respect to the longitudinal direction of the printed circuit board, wherein, in the first partial region, the first conductor track runs in the first layer, and the second conductor track runs in the second layer, and wherein, in the second partial region, the second conductor track runs in the first layer, and the first conductor track runs in the second layer. While a two-layer printed circuit board is advantageously more favorable and more flexible than a three-layer printed circuit board, it can ensure an electromagnetic shielding of the first conductor track, in which the measuring signal of the probe electrode is guided, only on one side. This is often sufficient. However, it is also possible for a first side of the printed circuit board to be located closest to the probe housing in a first partial region and a different, especially the opposite, side of the printed circuit board, in a second partial region, such that, in different partial regions, an electromagnetic shielding is necessary in different directions. Due to the division of the conductor track into two partial areas, wherein the two conductor tracks between the two partial areas allows the layer to be changed, this can be ensured according to the present disclosure. It goes without saying that, depending upon the current situation, the printed circuit board can also be subdivided into more than two partial areas, so that the direction of the shield changes more than once along the conductor track.

In a further embodiment, the wall of the module housing has at least one recess, which serves for the insertion of the flexible printed circuit board into the contacting module with an orientation perpendicular to its wall. This embodiment thus makes it possible to remove the printed circuit board laterally from the module housing. By choosing such a geometry, the diameter of the module housing and thus the space requirement of the contacting module can be reduced, compared to a variant without recesses. The wall of the module housing preferably has precisely two recesses, which are located opposite one another, wherein the printed circuit board is inserted into the contacting module through the first recess, and wherein, in the region of the second recess of the wall, is arranged, at least partially, the region of the printed circuit board which runs between the two contact regions. By folding the second contact region over the first, at least a part of the region of the printed circuit board projects between the two contact regions beyond the flat supporting element of the insulating sleeve. This must normally be taken into account when determining the radius of the module housing. However, if two recesses located on opposite sides of the module housing are integrated into the cylindrical wall of the module housing, the radius of the module housing can be minimized.

In a further embodiment, a fixing element is detachably applied to the module housing, which locks the flexible printed circuit board substantially in a plane and at least substantially closes a recess in the wall of the module housing. The use of a fixing element has two advantages. On the one hand, fixing the printed circuit board within the module housing permits the position of the contact regions of the printed circuit board to be essentially fixed on the two sections of the base body of the insulating sleeve. On the other hand, the integration of recesses within the wall of the module housing, in addition to the advantages already mentioned, also has a disadvantage, viz., that at least one recess reduces the electrical shielding effect of the module housing. However, by means of a suitable design of the fixing element, these recesses can be re-closed by the introduction of the latter, so that an overall good shielding effect can be achieved with a minimized space requirement.

It is thereby advantageous for the fixing element to be applied to the module housing by means of a press fit with a force closure. This allows a particularly simple fixation, without the need for separate parts for fixing.

In an embodiment, the thickness of the flat bearing element of the insulating sleeve is variable; in particular, the thickness, in a first base body facing the first region and in the end region facing away from the base body, is thicker than in the intermediary center region, and where the thickness of the end portion is maximally as large as that in the initial portion.

The position-dependent variation in the thickness, which is the extension of the insulating element in the direction parallel to the base body, serves to guide the printed circuit board from the first contact region into the second contact region in such a way that kinks in the printed circuit board are avoided as a result of the folding over of the contact regions and positioning within the housing module.

In a further embodiment, the probe electrode is free from the additional electrode in an end region projecting into the probe housing, wherein the contacting module is applied to the probe electrode in such a way that the second conductor track at least partially rests on the additional electrode. The contacting module then seats with a bottom side on the outer electrode in such a way that the contacting is made with the application of the contacting module to the probe electrode.

It is advantageous for the first fastening means to be a nut which is applied to the additional electrode, and/or for the second fastening means to be a nut which is applied to the probe electrode.

It is also advantageous for a resilient element or a co-spring-loaded resilient screw securing means to be arranged between the contacting module and the second fastening means. In this way, a constant force effect can be ensured by the fastening means, even in the case of thermal expansions.

Finally, it is advantageous for at least the housing module and the fixing element to be electrically conductive, for example, to be made of a metal.

BRIEF DESCRIPTION OF THE DRAWINGS

The present disclosure is described in more detail with reference to the following figures, FIG. 1 through FIG. 6. Illustrated are.

DETAILED DESCRIPTION

Figure 1:
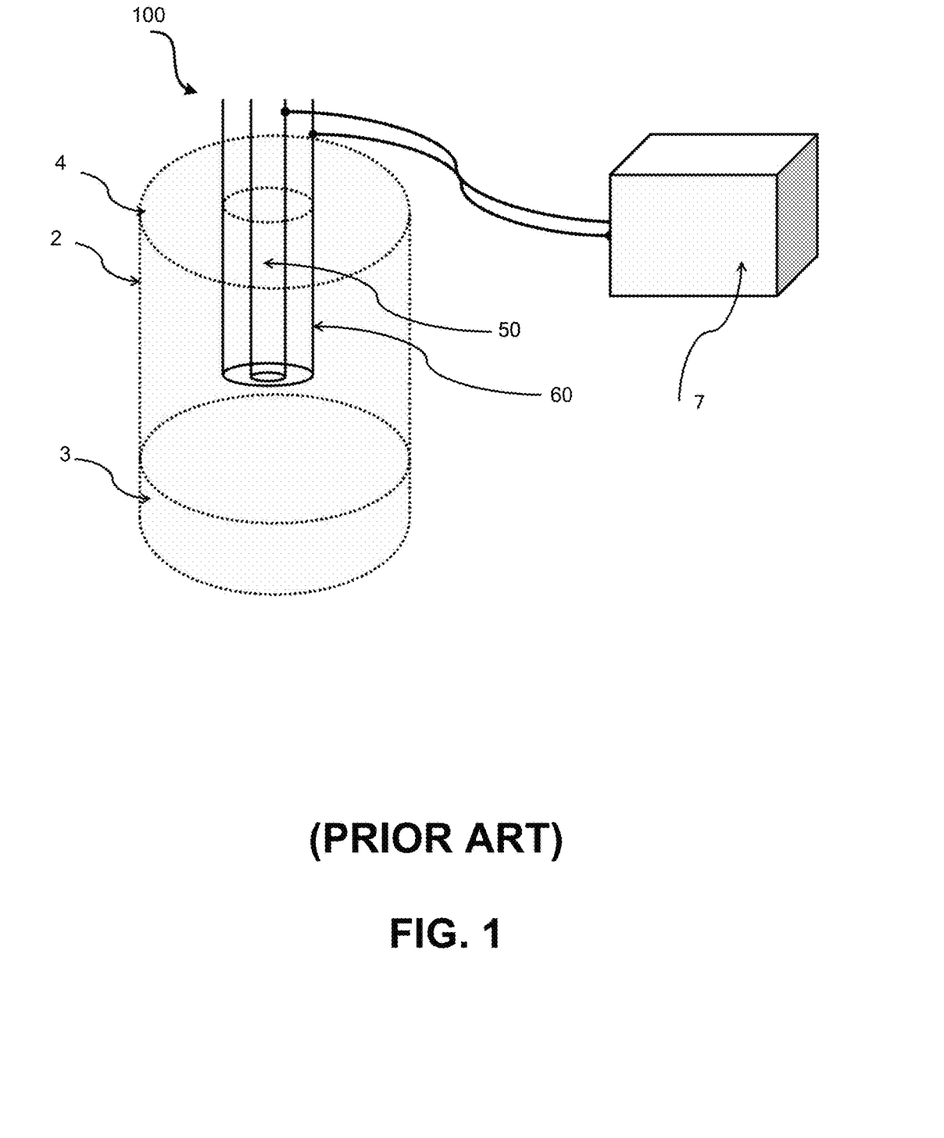
FIG. 1 shows a schematic representation of a measuring device suitable for the capacitive and/or conductive measuring method with a guard electrode according to the state of the art.

FIG. 1 shows a conventional probe unit 100 according to the state of art, by means of which a fill-level can be monitored in the capacitive and/or conductive mode of operation. Probe unit 100 is arranged on a container 2 having a wall 4 and partially protrudes into the same. Container 2, in turn, is at least partially filled with a medium 3. In the present example, the probe unit 100 is composed of a probe electrode 50 and an additional electrode 60 coaxially surrounding the probe electrode 50, the so-called conductor electrode, which serves to prevent deposit formation. The probe unit 100 is connected outside the container 2 to an electronic unit 7, which is responsible for the detection, supply, and/or evaluation of the signal. In particular, the electronic unit determines the fill-level of the medium 3 in the container 2 by means of a response signal received from the probe electrode 50. While in the example shown here the geometry of the probe unit 100 is selected in such a way that the probe electrode 50 and the additional electrode 60 partially extend into the container 2, it goes without saying that other configurations of the probe unit 100 with an at least section-wise coaxial structure fall under the present disclosure, for example, such probe units 100 as essentially terminate with the wall of the container 2, as with the FTW33 produced and distributed by the Applicant.

In embodiments according to the present disclosure, the probe electrode 5 and the conductor electrode 6 are contacted by means of an inventive contacting module for connection to the electronic unit 7. A selection of the conceivable embodiments of such a contacting module is shown in the following figures. However, it goes without saying that other embodiments not shown here are also conceivable, which also fall within the scope of the present disclosure.

Figure 2:
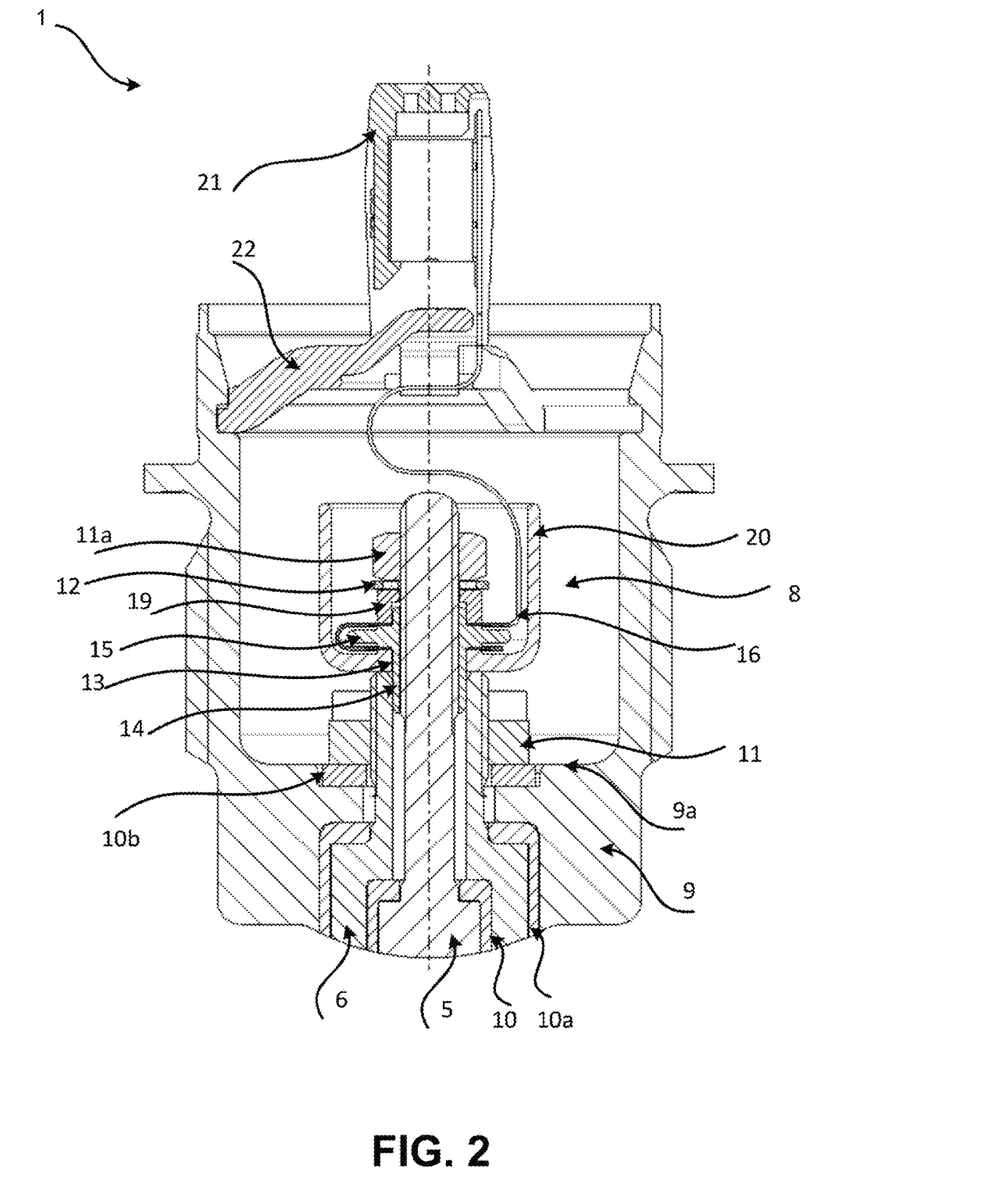
FIG. 2 shows the schematic structure of a first embodiment of a probe unit according to the present disclosure in a sectional view.

FIG. 2 shows a schematic construction of a section of a probe unit 1 with a first embodiment according to the present disclosure of a contacting module 8 according to claim 1 in a sectional view. A probe electrode 5, which serves for measuring the fill-level, protrudes with a rod-shaped section into a probe housing 9 and is coaxially surrounded by an additional (i.e., guard) electrode 6, to which the same potential is applied as the probe electrode 5. The probe electrode 5 and the additional electrode 6 are electrically separated from one another by an insulation 10. The additional electrode 6 is shorter in the axial direction of the housing interior than the probe electrode 5, so that the probe electrode 5 projects into the probe housing 9 via the additional electrode 6.

For the introduction of the probe unit 1 into the container 2 with the medium 3, the probe housing 9 can, for example, have a thread, by way of which it can be screwed into the wall 4 of the container 3 by means of a suitable sleeve. In addition to protecting the elements against environmental influences such as moisture deposits, probe housing 9 can also serve as a ground electrode. It is partially tubular in design and has a tapering 9a for affixing the probe electrode 5 and the additional electrode 6. The additional electrode 6 is separated from the probe housing 9 by means of a second insulation 10a. The unit consisting of the two electrodes 5, 6, the two insulators 10, 10a, and the probe housing 9 forms a coaxial structure, the axis of which is defined by the longitudinal axis of the probe housing 9.

Within the probe housing 9, a first fastening means in the form of a first nut 11 is applied to the tubular section of the additional electrode 6, which projects into the housing 9, and affixes the additional electrode 6 to the tapering 9a. A third insulation 10b provides for an electrical separation of the first nut 11, which is in electrically conductive contact with the additional electrode 6, from the probe housing 9. A second fastening means in the form of a second nut 11a is applied to the rod-shaped portion of the probe electrode 5 arranged in the probe housing 9 and can be tightened by means of a threaded engagement. The fastening of the second nut 11a causes a tightening force directed towards the housing interior on the elements of the axial structure and thus a fixed connection of the individual elements.

The contacting module 8 is, lastly, arranged between the additional electrode 6 and the second nut 11a. Advantageously, a resilient element 12 in the form of a toothed disc, or another co-braced resilient element, or a spring element, such as one or more disc springs or a spiral spring, is located between the contacting element 8 and the second nut 11a. Because of this measure, thermal expansion effects in the axial direction are compensated for. As a result, a permanent tightening force of the second nut 11a, and thus a permanent contact of the electrical contacts of the probe electrode 5 and the additional electrode 6 produced via the contacting module 8, are ensured. By the use of two nuts 11, 11a, the structure is also protected against twisting of one of the two nuts 11, 11a, as can occur, for example, when strong shocks or vibrations occur in the process.

The contacting module 8 has an insulating sleeve 13 with a cylindrical base body 14, a supporting element 15, and a flexible printed circuit board 16, wherein the contacting module 8 is connectible to the probe electrode 5 in a simple manner via the base body 14. The insulating sleeve 13 causes an exact centering of the rod-shaped section of the probe electrode 5 in the tubular section of the additional electrode 6 and prevents damage to the flexible printed circuit board 16 by a thread embedded in the rod-shaped section of the probe electrode 5. In addition, the insulating sleeve 13 ensures electrical separation between the additional electrode 6 and the probe electrode 5.

The flat support element 15 serves to support the two contact regions 16a, 16b (not shown here) of the flexible printed circuit board 16, which are preferably disc-shaped, with a central recess whose diameter is at least the diameter of the base body 14. The printed circuit board 16 is plugged onto the insulating sleeve 13 in such a way that the conductor tracks 17, 18 to be contacted (not shown here) are located on the side facing away from the supporting element 15. In this case, the support element 15 ensures that no short circuits can occur between the two contact areas 16a, 16b of the flexible printed circuit board 16.

On the first of the two contact regions 16a, 16b of the flexible printed circuit board 16, a first contact disc 19 follows which serves for the electrical contacting of the probe electrode 5 with the first conductor track 17 of the flexible printed circuit board 16 and can be applied to the first section of the base body 14 of the insulating sleeve 13. In the embodiment shown here, the first section is located on the short side and the second section is located on the long side of the base body 14. A module housing 20, in the form of a second contact disc with a wall, extending from the second contact disc and running parallel to the base body 14, which surrounds and protects the insulating sleeve 13 at least in the region of the support element 15 and the flexible printed circuit board 16 at least in the region of the contact regions 16a, 16b, and shields them in an electromagnetic manner from the probe housing 5, follows the second of the two contact regions 16b of the flexible printed circuit board 16 which is arranged in the second section of the base body 14. The module housing 20 thus has a pot-shaped geometry.

Both the module housing 20 and the first contact disc 19 are made of an electrically conductive material, for example, especially brass, copper, or stainless steel. The shaping of the first contact disc 19 and the second contact disc of the module housing 20 is adapted to that of the printed circuit board 16 and insulating sleeve 13. In the example shown here, it is disc-shaped, with a central recess. Furthermore, the outer diameter of the first contact disc 19 is smaller than that of the second contact disc.

The flexible printed circuit board 16 is led out at the top from the contacting module 8 and from the probe housing 9 so that an electronic unit can access it (not shown). For this purpose, a plug 21, which can be connected to a corresponding counterpart of the electronic unit, is applied to the free end region of the printed circuit board 16 which can be connected on the insulating sleeve 13. The plug 21 preferably has sockets for contacting the conductor tracks 18, 19, but can also have contact pins. A holding base 22 is connected to the plug 21 for affixing the plug 21 at a position provided. For example, the holding base 22 can be clamped into a groove in the probe housing 9.

Figure 3:
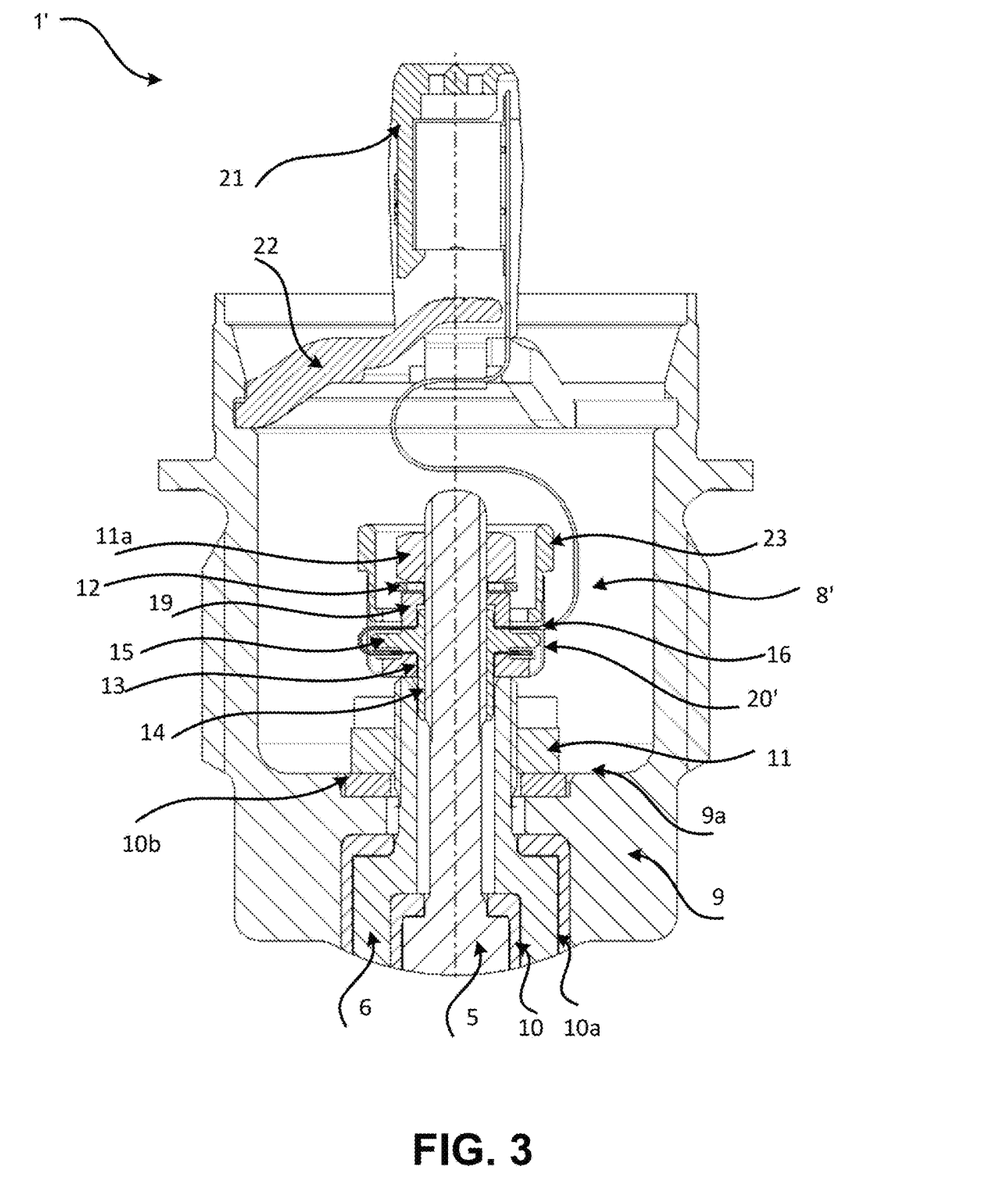
FIG. 3 shows the schematic structure of a second embodiment of a probe unit according to the present disclosure in a sectional view.

A second inventive embodiment of a contacting module 8' in a schematic configuration together with the analogous section of the probe unit 1 shown in FIG. 2 is the subject of the sectional view in FIG. 3. The reference character explained in conjunction with FIG. 2 will therefore not be discussed again here.

The essential difference between the embodiments in FIG. 2 and FIG. 3 relates to the contacting module 8 or 8', and is provided in that a fixing element 23 is integrated for the embodiment of the contacting module 8' shown in FIG. 3. The fixing element is releasably applied to a module housing 20' by means of a press fit with a force closure. For this reason, the design of the module housing 20' is also slightly modified. While the exact design of the module housing 20' will be described in detail in connection with FIG. 5, it should be noted here that the cylindrical wall of the module housing 20' is shortened in contrast to the embodiment as shown in FIG. 2. Furthermore, the wall of the module housing 20' has two recesses. From the first recess, the flexible printed circuit board 16 is led out of the module housing 20' laterally. The region of the flexible printed circuit board 16, which is located between the two contact regions 16a, 16b, protrudes from the second recess.

Finally, FIG. 4 shows a once again slightly modified embodiment of the contacting module 8", but in a view rotated by 90° in comparison with FIGS. 2 and 3. Again, no reference is made to the reference numerals already described. On the one hand, the position of the fixing element 23 on the module housing 20' is more clearly visible in this view. The cylindrical wall of the fixing element 23 extends partly into the wall of the module housing 20' and thus locks the flexible printed circuit board 16 in the two sections of a flat supporting element 15'.

Figure 4:
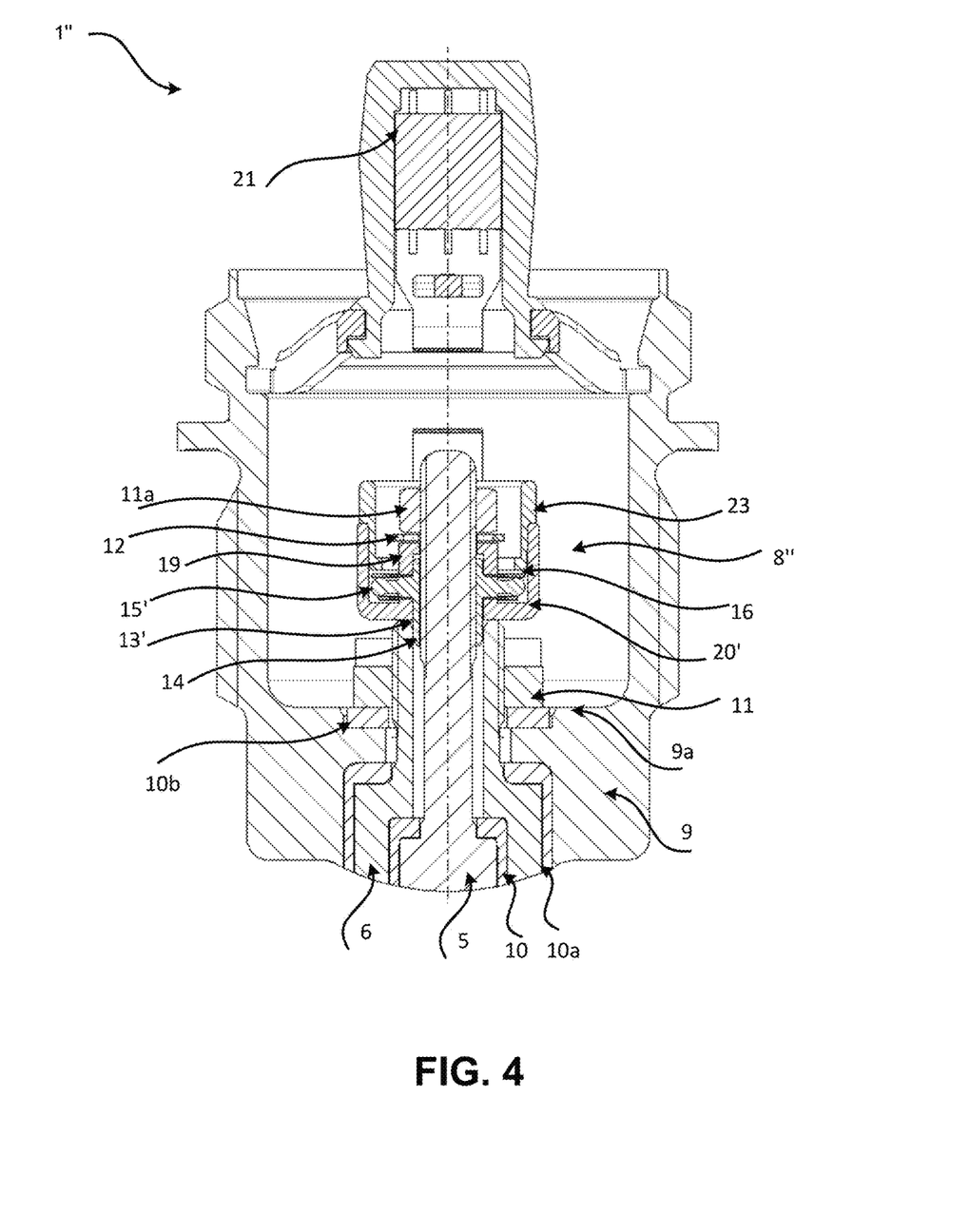
FIG. 4 shows the schematic structure of a third embodiment of a probe unit according to the present disclosure in a sectional view.

However, the actual difference between the embodiment shown in FIG. 4 and the previous embodiments relates to the design of the insulating sleeve 13'. The flat supporting element 15' of the insulating sleeve 13' is, in fact, of variable thickness, so that it has a smaller thickness in an intermediate region between the region facing the base body 14 and the end region. As a result, the region extending between the two contact regions 16a, 16b of the flexible conductor track 16 is guided and protected against kinking.

Figure 5A:
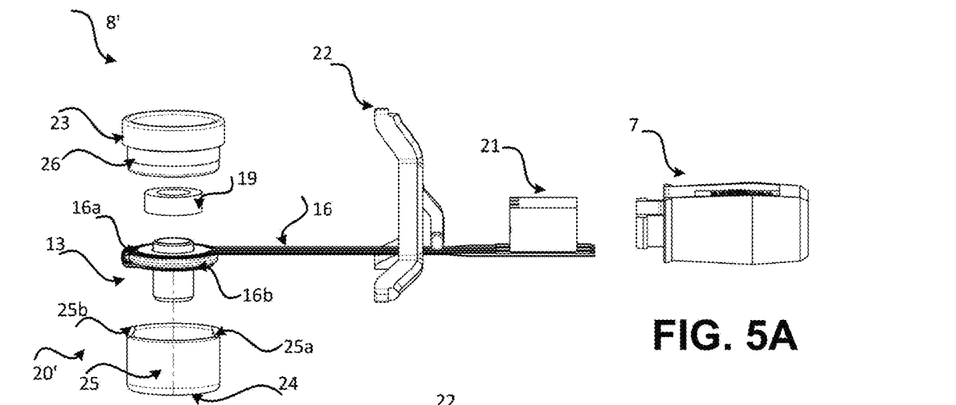
FIGS. 5A-5C show detailed views of a contacting module according to the third embodiment in: (A) an exploded view, (B) a sectional view, and (C) a perspectival view.
Figure 5B:
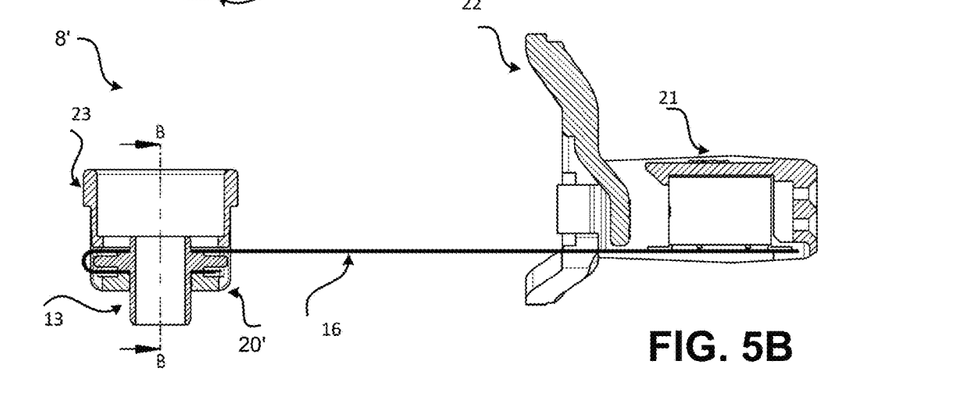
Figure 5C:
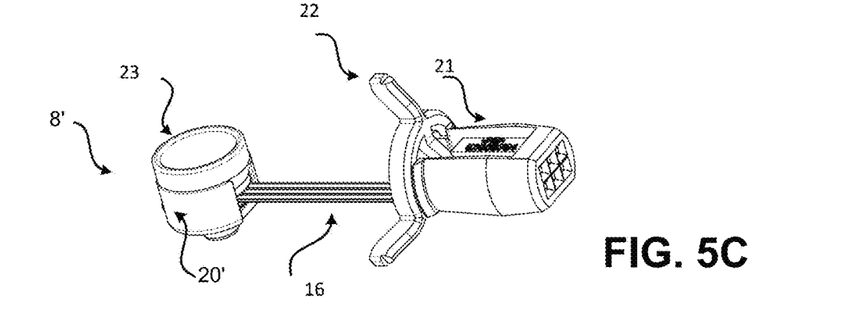

Finally, FIGS. 5A-5C shows a detailed view of a contacting module 8' in the same embodiment as that shown in FIG. 3.

In the exploded view in FIG. 5A, the module housing 20' with a pot-shaped geometry is shown with the first contact disc 19, and the second contact disc 24 and the cylindrical wall 25 with a first 25a and a second 25b recess. Above the second contact disc 24, the insulating sleeve 13 is located with the base body 14 and the flat supporting element 15. This is preferably constructed as an injection-molded or turned part made of plastic. In this case, the first contact region 16a of the flexible printed circuit board 16 is located in the first region (the region facing the short side of the insulating sleeve 13) of the supporting element 15, and the second contact region 16b of the flexible printed circuit board 16 is located in the second region (the region facing the long side of the insulating sleeve 13) of the supporting element 15, such that, in fact, the first and second conductor tracks are located on the side facing away from the flat supporting element 15. The first contact region 16a is contacted by the first contact disc 19, and the second contact region 16b is contacted with the cylindrical wall 25 by means of the second contact disc 24. Finally, following the cylindrical wall 25 is the fixing element 23, which can be applied by press fit with a force closure to the module housing 20', and the recesses 25a, 25b of the module housing 20', up to the region in which the flexible printed circuit board 16' is lead out laterally from the module housing 20', and the region in which the region of the flexible printed circuit board extends between the two contact regions 16a and 16b protrudes beyond the wall of the module housing 20'.

Furthermore, the plug 21 for connecting to the electronics unit 7, which is indicated by the socket belonging to the plug 21, and the holding base 22 are shown in the second end region of the flexible printed circuit board 16.

FIG. 5B shows a two-dimensional sectional drawing of the contacting module 8' from FIG. 5A. For the sake of clarity, not all parts are marked with a reference numeral. It is important to note that the first contact disc 19 (not shown here; see FIG. 5A) contacts the first contact area 16a of the flexible printed circuit board 16 in the first section of the supporting element 15, and that the module housing 20' contacts the second contact area 16b of the printed circuit board 16 by means of the second contact disc 24. In this view, it can be seen particularly well that the fixing element 15, in addition to the partial closing of the recesses 25a, 25b, fixes the printed circuit board 16 within the module housing 20' and essentially arrests it in a plane such that the position of the contact areas 16, 16a of the printed circuit board 16 are fixed on the two sections of the base body 14 of the insulating sleeve 13.

A perspective illustration of the contacting module 8' with the flexible printed circuit board 16 is, lastly, shown in FIG. 5C. The flexible printed circuit board 16 is led out laterally from the contacting module 8' and opens in its second end region in a plug 21 with a holding base 22. Through the use of a module housing 20' with two recesses 25a, 25b and a fixing element 23, the contacting module 8' is fixedly connected to the printed circuit board 16.

Figure 6A:
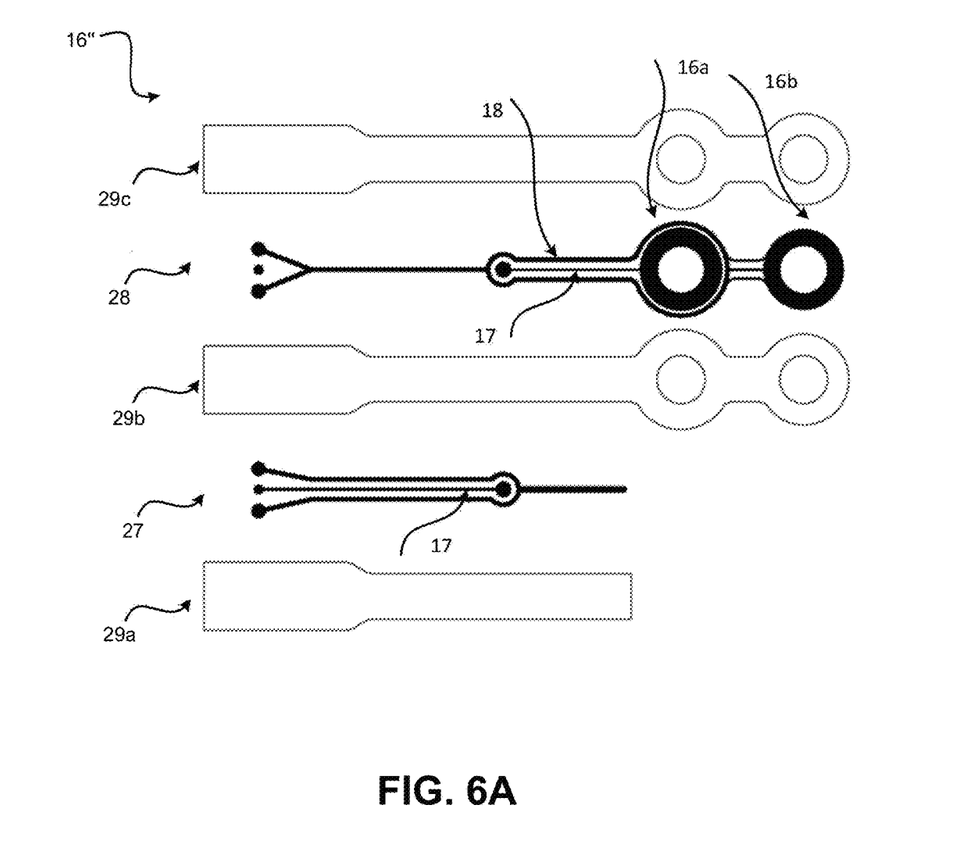
FIGS. 6A and 6B show embodiments of a flexible printed circuit board in (A) a two-layered and (B) a three-layered design.
Figure 6B:
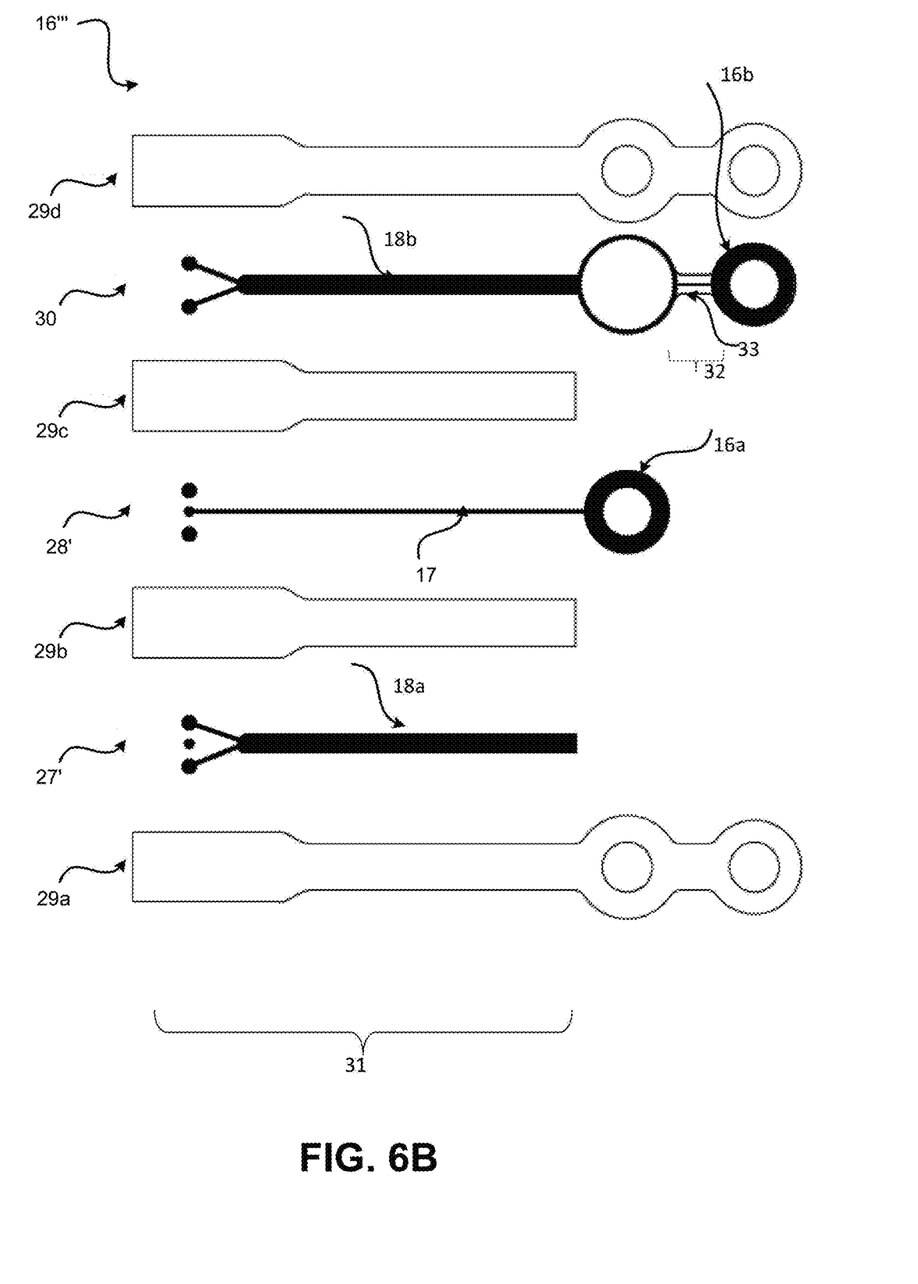

FIG. 6 shows two examples of a printed circuit board 16 according to the present disclosure.

Irrespective of the number of positions for the flexible conductor track 16, care must be taken that the second conductor track 18 in each case ensures a good electrical shielding of the first conductor track 17. Ideally, the second conductor track 18 must therefore be wider than the first conductor track. However, in order to keep capacitive disturbances to the measuring signal as low as possible, and, accordingly, to influence the measuring signal as little as possible, the two conductor paths should be designed as narrow as possible.

FIG. 6A shows a two-layer printed circuit board 16". The individual layers are arranged one above the other in a sectional view. The printed circuit board 16 has a first layer 27 and a second layer 28. Below the first layer 27, above the second layer 28, as well as between the first 27 and second layers, plastic layers 29a, 29b, 29c are arranged to insulate the first 27 and second 28 layers from each other and from the environment. Within the first layer 27, the first conductor track 17 runs at least in sections, and the second conductor track 18 at least sectionally within the second layer 28. In this example, the conductor tracks 17, 18 change the layers 27, 28 section-by-section, in which they run in each case.

FIG. 6B shows a three-layer printed circuit board 16" in the same display mode. The printed circuit board 16" has a first layer 27', a second layer 28', and a third layer 30. Again, plastic layers 29a', 29b', 29c', 29d' is arranged below the first layer 27', in each case between two layers 27', 28' and above the third layer 30. The first conductor track 17 runs in the second layer 28'. The second conductor track 18, on the other hand, is at least divided into two branches in a partial section namely, into a first branch 18a and a second branch 18b. In the example shown here, the second conductor track 18 is, for example, divided into the two branches 18a and 18b in the region 31 up to the two contact regions 16a, 16b, wherein the first branch 18a of the second conductor track 18 runs in the first layer 27, and wherein the second branch 18b of the second conductor track 18 runs in the third layer 30. In a region 32 between the two contact regions 16a and 16b, on the other hand, the flexible printed circuit board 16" is designed to be thinner. This region 32 is bent when the printed circuit board 16" is folded over for the purpose of covering the two contact regions 16a and 16b on the two sections of the base body 14 in the same manner. The thinner design makes this area lighter, so that a higher flexibility is present, which is at least desirable for the region 32. In addition, an electrical line 33 in the region 32 is designed redundantly in the form of three parallel line branches, each line branch having a smaller diameter than the remaining line. Even damage to the region 32 between the two contact regions 16a and 16b is harmless for the measurement, since, in the region 32, only the second conductor track 18 runs, which serves to make contact with the additional electrode or guard electrode 6.

The invention claimed is:

1. A probe unit comprising:
   a probe housing;
   a probe electrode being generally rod-shaped and disposed in the probe housing;
   a guard electrode at least partially coaxially surrounding the probe electrode and electrically isolated from the probe electrode by electrical insulation;
   a first fastening means affixing the guard electrode in the probe housing;
   a contacting module applied to a rod-shaped section of the probe electrode and disposed in the probe housing; and
   a second fastening means affixing the contacting module to the probe electrode,
   wherein the contacting module comprises:
      an insulating sleeve having a substantially cylindrical base body structured to receive a portion of the probe electrode and a support element, which extends substantially orthogonal to the base body and divides the base body into a first section and a second section;
      a flexible printed circuit board including a first conductor track structured to electrically contact the probe electrode and a second conductor track structured to electrically contact the guard electrode, the circuit board further including, in an end region, a first contact region into which the first conductor track opens and a second contact area into which the second conductor track opens, wherein the first contact region and the second contact region each have a central recess whose diameter is at least equal to an outer diameter of the base body of the insulating sleeve, and wherein at least the central recesses of the first contact region and the second contact region are formed by folding the circuit board such that the first contact region can be applied to the first portion of the base body and the second contact region can be applied to the second portion of the base body; and
      a module housing including a first contact disc applied to the first section of the base body of the insulating sleeve as to electrically contact the first conductor track in the first contact region, and including a second contact disc applied to the second section of the base body of the insulating sleeve as to electrically contact the second conductor track in the second contact region,
   wherein the module housing has a generally pot-shaped geometry, with a cylindrical wall which extends parallel to the base body from the second contact disc, which wall has at least the probe electrode in the region in which the contacting module is applied, the insulating sleeve is arranged at least in the region of the support element, and the circuit board substantially surrounds, protects, and/or shields against electromagnetic radiation in the region of the first and second contact regions, and wherein the first contact disc has a smaller outer diameter than the second contact disc.

2. The probe unit of claim 1, wherein the flexible printed circuit board is a semiflexible printed circuit board having at least two layers, a first layer in which the first conductor runs at least in sections and a second layer in which at least the second conductor track runs at least in sections.

3. The probe unit of claim 1, wherein the flexible printed circuit board is a three-layer circuit board with a first layer, a second layer and a third layer, wherein the second layer is arranged between the first layer and the third layer, wherein the first conductor track runs in the second layer, wherein the second conductor track at least in the region up to the first and second contact regions is subdivided into a first branch and a second branch, and wherein the first branch of the second conductor track runs in the first layer, and the second branch of the second conductor track runs in the third layer.

4. The probe unit of claim 1, wherein the flexible printed circuit board is a two-layered printed circuit board with a first layer and a second layer, and first and second partial areas with respect to the longitudinal direction of the printed circuit board, wherein in the first partial area the first conductor track runs in the first layer, and the second conductor track runs in the second layer, and wherein in the second partial area the second conductor track runs in the first layer, and the first conductor track runs in the second layer.

5. The probe unit of claim 1, wherein the wall of the module housing has at least one recess enabling the insertion of the flexible printed circuit board into the contacting module with an orientation perpendicular to the wall.

6. The probe unit of claim 5, wherein the wall of the module housing has two recesses, located opposite one another, wherein the printed circuit board is inserted into the contacting module through the first recess, and wherein in the region of the second recess is arranged, at least partially, the region of the printed circuit board that runs between the first and second contact regions.

7. The probe unit of claim 5, wherein the support element of the insulating sleeve has a variable thickness such that the thickness in a first base body facing the first region and in the end region facing away from the base body is thicker than in the intermediate center region, and wherein the thickness of the end portion is maximally as large as that in the initial region.

8. The probe unit of claim 7, wherein the fixing element is applied to the module housing by a press fit with force closure.

9. The probe unit of claim 1, further comprising a fixing element detachably applied to the module housing, the fixing element structured to lock the flexible printed circuit board substantially in a plane and to substantially close a recess in the wall of the module housing.

10. The probe unit of claim 1, wherein the probe electrode is free from the guard electrode in an end region projecting into the probe housing, and wherein the contacting module is applied to the probe electrode such that the second conductor track at least partially seats on the guard electrode.

11. The probe unit of claim 1, wherein the first fastening means is a nut that is applied to the guard electrode and/or the second fastening means is a nut that is applied to the probe electrode.

12. The probe unit of claim 1, wherein a resilient element or a co-spring-loaded resilient screw is arranged between the contacting module and the second fastening means.

13. The probe unit of claim 1, wherein the module housing and the fixing element are electrically conductive.

* * * * *